US00PP15531P3

(12) United States Plant Patent
Redman

(10) Patent No.: US PP15,531 P3
(45) Date of Patent: Feb. 8, 2005

(54) ***CHRYSANTHEMUM* PLANT NAMED 'SPRITZA TIME YELLOW'**

(50) Latin Name: *Chrysanthemum morifolium*
Varietal Denomination: Spritza Time Yellow

(75) Inventor: Ruth Redman, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 0 days.

(21) Appl. No.: 10/365,156

(22) Filed: Feb. 11, 2003

(65) Prior Publication Data

US 2004/0158907 P1 Aug. 12, 2004

(51) Int. Cl.[7] ..... A01H 5/00
(52) U.S. Cl. ..... Plt./295
(58) Field of Search ..... Plt./295

(56) References Cited

U.S. PATENT DOCUMENTS

PP8,694 P 4/1994 Hesse ..... Plt./295

OTHER PUBLICATIONS

Brummitt, 1997. The Garden, Horticultural Science: Chrysanthemum once again, pp. 662–663.*
1998 Ficor catalog, listing the variety 'Ingot Time.' See, e.g., p. 4.
1999 Ficor catalog, listing the variety 'Ingot Time.' See, e.g., p. 4.
2000 Ficor catalog, listing the variety 'Ingot Time.' See, e.g., p. 4.
2001 Ficor catalog, listing the variety 'Ingot Time.' See, e.g., p. 4.
2002 Ficor catalog, listing the variety 'Ingot Time.' See, e.g., p. 4.

* cited by examiner

*Primary Examiner*—Anne Marie Grunberg
*Assistant Examiner*—June Hwu
(74) *Attorney, Agent, or Firm*—Howrey Simon Arnold & White LLP

(57) ABSTRACT

A new variety of *Chrysanthemum* plant named 'Spritza Time Yellow,' having sunny yellow medium anemone flowers with a flat capitulum canopy. The variety is upright and free branching with a good foliage presentation.

1 Drawing Sheet

Latin name of the genus and species: Botanical classification: *Chrysanthemum morifolium.*

Variety denomination: The new *Chrysanthemum* variety denomination is 'Spritza Time Yellow.'

BACKGROUND OF THE INVENTION

The present invention comprises a new and distinct cultivar of *Chrysanthemum* botanically known as *Chrysanthemum morifolium,* and referred to by the cultivar name 'Spritza Time Yellow.'

'Spritza Time Yellow,' identified as 21703-0, originated from a cross made in a controlled breeding program in Vinnetrow Road, Chichester, West Sussex, United Kingdom. The female parent of the new variety is the unpatented variety known as 'Ingot Time.' The male parent of the new variety is an undistributed, unpatented seedling identified as '21170-2.' The new variety 'Spritza Time Yellow' has been asexually reproduced by vegetative cuttings in Chichester, West Sussex, United Kingdom and the distinguishing characteristics are retained through successive generations of asexual reproduction.

BRIEF SUMMARY OF THE INVENTION

'Spritza Time Yellow' is a pot type of *Chrysanthemum* plant variety having sunny yellow anemone flowers with a light green disc.

Comparison with Female Parent

Plants of the new *Chrysanthemum* variety 'Spritza Time Yellow' are similar to the parent 'Ingot Time' in plant habitat and growth rate. In side-by-side comparisons in Chichester, West Sussex, United Kingdom, under commercial practice, plants of the new *Chrysanthemum* variety 'Spritza Time Yellow' differed from plants of the parent 'Ingot Time' in the following characteristics.

1. The new variety 'Spritza Time Yellow' produces medium sunny yellow anemone flowers whereas the parent 'Ingot Time' produces small golden yellow anemone flowers.
2. Plants of the new variety 'Spritza Time Yellow' have larger and taller inflorescence than plants of the parent 'Ingot Time.'

Comparison with Male Parent

Plants of the new *Chrysanthemum* variety 'Spritza Time Yellow' are similar to the male parent '21170-2' in plant habitat and growth rate. In side-by-side comparisons in Chichester, West Sussex, United Kingdom, under commercial practice, plants of the new *Chrysanthemum* variety 'Spritza Time Yellow' differed from plants of the parent '21170-2' in the following characteristics.

1. The new variety 'Spritza Time Yellow' produces medium sunny yellow anemone flowers whereas the male parent '21170-2' produces large golden yellow single flowers.
2. Plants of the new variety 'Spritza Time Yellow' have smaller and shorter inflorescence than plants of the male parent '21170-2'.

Comparison with Other Varieties

Plants of the new *Chrysanthemum* variety 'Spritza Time Yellow' are dissimilar to 'Golden State,' U.S. Plant Pat. No. 8,694, in plant habitat and growth rate. However, in side-by-side comparisons in Chichester, West Sussex, United Kingdom, under commercial practice, plants of the new *Chrysanthemum* variety 'Spritza Time Yellow' compare to the plants of 'Golden State' in the following characteristics.

1. The new variety 'Spritza Time Yellow' produces medium sunny yellow anemone flowers whereas 'Golden State' produces large golden yellow anemone flowers.
2. Plants of the new variety 'Spritza Time Yellow' have smaller and shorter inflorescence than plants of 'Golden State.'
3. The new variety 'Spritza Time Yellow' has a response time of 8 weeks whereas 'Golden State' has a response time of 8.5 weeks.

BRIEF DESCRIPTION OF ILLUSTRATION

Typical specimens of the plant and flowers for the new *Chrysanthemum* variety 'Spritza Time Yellow' are shown in the accompanying digital photograph. The colors shown are as true as possible within the usual limits of this kind of illustration.

FIG. 1 is a whole plant view of the new variety 'Spritza Time Yellow' grown in a pot. The plant shown in the illustration is 56 days from the commencement of Short Days.

DETAILED BOTANICAL DESCRIPTION

The following description of the new *Chrysanthemum* variety 'Spritza Time Yellow' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum*.

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 28 days with a response time of about 8 weeks. The new variety is suitable for growth in a temperature range of 15° C. to 25° C.

The new variety may be produced as a spray. The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright.
Height: 28 cm.
Width: 32 cm.
Branching characteristics: Upright and free branching.
Length of lateral branches: 13 cm.
Diameter of lateral branches: 0.6 cm.
Surface of lateral branches: Slightly pubescent.
Number of breaks from pinch: 6.
Stem color: 138B.
Response time: 54 days.
Vigor: Medium tall.
Shelf life: 28 days.
Disease/pest (susceptibility/resistance observed): None observed to date.
Growth retardant type and treatment: 3 applications of 2.5 gm/liter B9 @2, 21 and 28 days after sticking unrooted cuttings.

The plants were grown for 2 weeks in Long Day conditions (20 hours of light) and then transferred to Short Day conditions (13 hours of dark).

Propagation:
*Type.*—Vegetative propagation via stem cuttings.
*Time to rooting.*—14 days with soil temperatures of 18° C.
*Rooting habit.*—After 7 days the first roots emerge and form root primordia. In 14 Long Days a complete root system is developed.

Foliage

Number of leaves per lateral branch: 8.
Compound or single: Single.
Arrangement of leaves: Alternate.
*Shape of leaf.*—Typically 5 lobed.
*Leaf of size.*—Width (cm): 7.5. Length (cm): 6.
*Leaf apex.*—Acute.
*Base: Cordate.*
*Attachment.*—Petioled.
*Aspect.*—Slightly undulating.
*Margin.*—Lobed.
*Surface characteristics.*—Top: slightly pubescent. Bottom: pubescent.
Petiole:
*Color.*—137B.
*Length.*—2.5 cm.
*Diameter.*—0.2 cm.
*Surface.*—Slightly pubescent.
Venation: Net prominent mid vein at underside.
*Color.*—Upper side: near 138A. Under side: near 138A.
Color:
*Mature leaf, upper side.*—near 137A; under side: near 137C.
*Young leaf, upper side.*—near 139A; under side: near 137B.

Flower

Flower appearance: Matte.
Flower type: Anemone.
Flower form: Flat.
Flower shape: Round.
Flowering habit: Flat capitulum.
Number of blossoms per branch: 3.
Inflorescence form: Cyme.
*Depth of fully expanded blossoms.*—1 cm.
*Diameter of fully expanded blossoms.*—5 cm.
*Anemone center diameter.*—1.8 cm.

Phyllaries:
*Number.*—30.
*Color.*—Near 138B.
*Length.*—0.6 cm.
*Width.*—0.2 cm.
*Texture/appearance.*—Pubescent.
Peduncle: Peduncle length is shortest at the terminal flower and progressively longer moving down the stem.
*Length.*—13 cm (average).
*Diameter.*—0.6 cm.
*Color.*—Near 138B.
*Surface.*—Slightly pubescent.
*Habit.*—Slightly curving.
*Strength.*—Moderately strong.
Pedicel:
*Length.*—Terminal: 4 cm; lateral: 5.5 cm.
*Color.*—Near 138B.
*Diameter.*—0.3 cm.
*Surface.*—Slightly pubescent.
*Habit.*—Slightly curving.
*Strength.*—Moderately strong.
Ray florets:
*Form/shape.*—Straight and spatulate with oblong shape.
*Texture/appearance.*—Matte.
*Number per flower.*—30.
*Length.*—2 cm Width: 0.6 cm.
*Apex.*—Rounded.
*Base.*—Tapered.
*Margin.*—Entire.
Disc florets:
*Form/shape.*—Cylindric.
*Texture/appearance.*—Shiny.
*Number per flower.*—250.
*Length.*—0.6 cm; Width: 0.1 cm.
*Diameter of disc.*—1.8 cm.
Fragrance: None observed.

Flower bud (at onset of color):
*Length.*—0.7 cm.
*Diameter.*—1 cm.
*Form/shape.*—Globular.
General flower color:
*1. Ray florets, upper side.*—13B. Immature: near 13B. Mature: near 13B. Older/Fading: near 13C.
*2. Ray florets, under side.*—12B. Immature: near 12A. Mature: near 12B. Older/Fading: near 12C.
*3. Disc florets.*—Immature: near 145B. Mature: near 145B. Older/Fading: near 9B.
*4. Bud.*—12B.
Flower progression with age: There is no change with the flowers form, but there is a slight color fading with age.
Lastingness of blooms: About 28 days.

Reproductive Organs

Gynoecium. Present on Ray and Disc florets.
Ray florets per individual flower:
*Pistil number.*—30.
*Stigma color.*—Near 6A.
*Stigma shape.*—Forked.
*Style color.*—Near 3C.
*Style length.*—0.2 cm.
Disc florets per individual flower:
*Pistil number.*—250.
*Stigma color.*—Near 6A.
*Stigma shape.*—Forked.
*Style color.*—Near 3C.
*Style length.*—0.2 cm.
Androecium: Not observed.
Fruits and seeds: None observed.

What is claimed is:

1. A new and distinct variety of *Chrysanthemum* plant, substantially as described and illustrated herein.

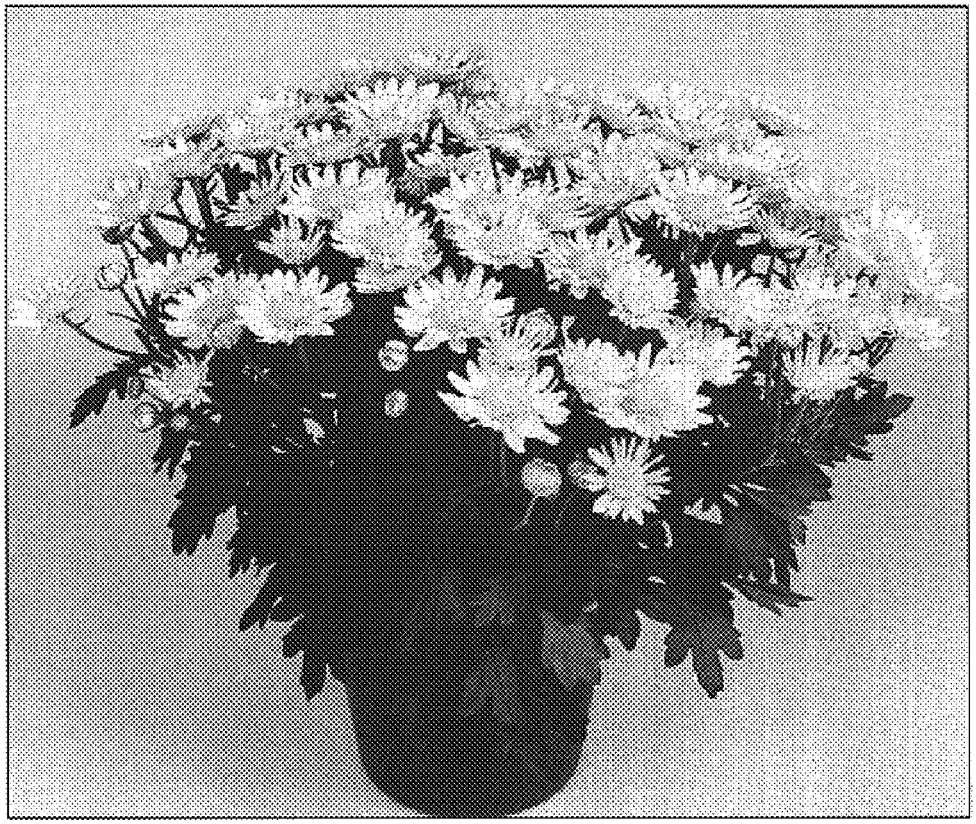

* * * * *